United States Patent

Novosel

[11] Patent Number: 5,975,120
[45] Date of Patent: Nov. 2, 1999

[54] AUTOMATICALLY RETRACTABLE GAS TUBING FEED SPOOL

[76] Inventor: Lorraine Ley Novosel, 2610 Siesta Dr., Pittsburgh, Pa. 15241

[21] Appl. No.: 09/035,043

[22] Filed: Mar. 5, 1998

[51] Int. Cl.⁶ ................................................. B65H 75/34
[52] U.S. Cl. ........................ 137/355.23; 137/355.26; 137/377
[58] Field of Search .............. 137/355.16, 355.23, 137/355.26, 377

[56] References Cited

U.S. PATENT DOCUMENTS

| | | | |
|---|---|---|---|
| 3,822,719 | 7/1974 | Nederman | 137/355.26 |
| 4,543,982 | 10/1985 | Wolfe | 137/355.23 |
| 4,685,634 | 8/1987 | Schwartz | 242/96 |
| 5,236,143 | 8/1993 | Dragon | 242/107 |
| 5,392,808 | 2/1995 | Pierce | 137/355.23 |
| 5,518,023 | 5/1996 | Garcia | 137/355.26 |
| 5,666,992 | 9/1997 | Robins | 137/355.23 |
| 5,678,596 | 10/1997 | Corallo | 137/355.23 |
| 5,787,923 | 8/1998 | Shea et al. | 137/355.23 |
| 5,794,648 | 8/1998 | Jentzsch et al. | 137/355.23 |
| 5,848,642 | 12/1998 | Sola | 137/355.16 |

*Primary Examiner*—A. Michael Chambers
*Assistant Examiner*—Thomas L. McShane
*Attorney, Agent, or Firm*—Kenneth P. McKay, Esq.

[57] ABSTRACT

A means of automatically dispensing air tubing on demand of the user, then retracting it, upon signal by the user. The spool is highly portable and conducive to use in a non-hospital environment because of its simplicity and ease of operation. As the user translates, the air tubing length between the user is increased. As the user moves toward the air supply, the tubing can be retracted. The instant invention may be fastened to a wheelchair or may be carried on the person of the user to facilitate its employment.

4 Claims, 6 Drawing Sheets

AUTOMATICALLY RETRACTABLE GAS TUBING FEED SPOOL

BACKGROUND OF THE INVENTION

1. Field of the Invention

The present invention is an accessory for use by individuals who must rely on oxygen therapy to provide them with a greater degree of mobility, safety and comfort. The device is a portable and inexpensive, automatically retractable gas tubing feed spool. It provides a means of automatically dispensing air tubing, on demand of the user, then retracting it, upon signal by the user.

Many persons rely on oxygen for medical treatment. Ambulatory persons who are not confined to bed most often find it difficult to contend with 25 to 50 feet of air tubing as they move about. Air supplies are contained within heavy tanks, which cannot be as mobile as the user. By providing a convenient means of controlling the dispensation of the tubing, an improvement in medical treatment can be realized.

The instant invention may be fastened to a wheelchair, attached to a walker or may be carried by the user to facilitate its employment. It acts as an intermediary between the mobile user and the immobile air supply. As the mover translates, the air tubing length between the user is increased. As the user moves toward the air supply, the tubing can be retracted.

The instant invention may be fastened to a wheelchair or may be carried on the person of the user to facilitate its employment.

2. Description of the Related Art

The Prior Art encompasses a variety of reel type devices for wire, cable and other cord-type products. Also included are reels for intravenous feeding apparatus for use with tubing, including reels for spool and retraction mechanisms. Hospitalization for some patients sometimes requires that the patient receive oxygen therapy for conditions which result from oxygen deficiency. There exist retractable tubing reels employed in conjunction with an oxygen supply tank and nasal oxygen catheter for use in hospitals. Those devices facilitate the conveyance of the oxygen through tubing apparatus that allows for retraction of the tubing. See, e.g., U.S. Pat. No. 5,392,808 (Pierce).

The Prior Art does not include devices, which provide for portability and cleanliness outside the hospital environment. Specifically, the devices, and reasonable combinations thereof, show the art restricted to heavy and fixed devices, which do not serve the ambulatory patient in the setting of the home, office or public facilities. This is particularly relevant in the times of expanding home health care where hospitalization is being minimized. It is also particularly relevant in these times of the expanding numbers of elderly, those most often susceptible to respiratory ailments. There exists, then, the need for such a device that is encompassed in the present invention, and not in the Prior Art or the reasonable extensions thereof

PRIOR ART

U.S. Pat. No. 5,392,808 Feb. 28, 1995, a retractable tubing reel device utilized in conjunction with a oxygen supply tank and a nasal oxygen catheter, the device having an extended length of tubing allowing a patient greater movement beyond the immediate area of the oxygen tank and being retractable therein. The device is attached at or in proximity to the supply and is not movable with the user or otherwise portable.

U.S. Pat. No. 5,236,143 (Dragon) dated Aug. 17, 1993, a unitary housing contains a spring-biased return spool with the spool including a pre-determined length of intravenous feed conduit wound thereof There are guide roller structures mounted to the forward and rear walls of the housing to guide the tube directed there through.

U.S. Pat. No. 4,685,634 (Schwartz) dated Aug. 11, 1987, an extension cord reeling mechanism having electrical or telephone jacks. The reeling member has a cover having mounted to it a mechanism to connect an extension cord and allow the extension cord to pass through the housing and be retracted.

U.S Pat. No. 5,518,023 (Garcia) shows a hose coiling apparatus for an acetylene tank having a regulator, a hose and an operating handle. The apparatus comprises a structure for safely storing the hose in a wound up manner. A facility is for mounting the storing structure onto the acetylene tank. A person can grip the operating handle and pull the hose out of the storing structure for use, thereby preventing the hose from getting tangled, pinched and pulled accidentally.

U.S Pat. No. 5,678,596 (Corallo) teaches a retractable garden hose apparatus comprising a reel assembly mounted to a ceiling joist within a basement adjacent an exterior wall, allowing the hose to be drawn through the wall for use, and further comprising a retractable reel for re-winding the hose.

U.S Pat. No. 5,666,992 (Robins) demonstrates, in the art, an air hose reel formed by an upright L-shaped support horizontally journaling an axle having reel forming spokes secured to one end portion for angular rotation in a vertical plane. A tension spring and friction washer surround the axle for retarding free wheeling movement of the reel. Couplings at respective ends of the axle are connected with air hose.

SUMMARY OF THE INVENTION

The objective of the present invention is to provide a lightweight and portable retractable gas tubing feed spool thereby demonstrating a marked improvement in the art of retractable air tubing devices.

A secondary objective is to provide such portability that the spool may be mobile with the patient or with the appurtenances used by the patient.

A third objective is to provide easy attachment and removability such that it can accommodate a variety of locations and appurtenances.

A fourth objective is to provide a reasonably priced accessory such that all patients under treatment can utilize the invention.

A fifth objective is to provide a device which can utilize any known band of oxygen tubing and is easily assembled, maintained and cleaned by the user, outside the hospital environment, thereby facilitating its use in homes and care facilities.

A sixth objective is to provide he oxygen therapy user with greater safety by containing excess oxygen tubing thereby reducing the likelihood of injury due to tripping or falling over the tubing that is resting on the floor.

A seventh objective is to provide a device that would prevent kinking, twisting and tangling of the tubing, thus reducing the risk of stopping the flow of vital oxygen to the user.

DETAILED DESCRIPTION OF THE PREFERRED EMBODIMENT

The invention will now be described in detail in relation to a preferred embodiment and implementation thereof which is exemplary in nature and descriptively specific as disclosed. As is customary, it will be understood that no limitation of the scope of the invention is thereby intended, and that the invention encompasses such alterations and further modifications in the illustrated device, and such further applications of the principles of the invention illustrated herein, as would normally occur to persons skilled in the art to which the invention relates.

Figure 1:
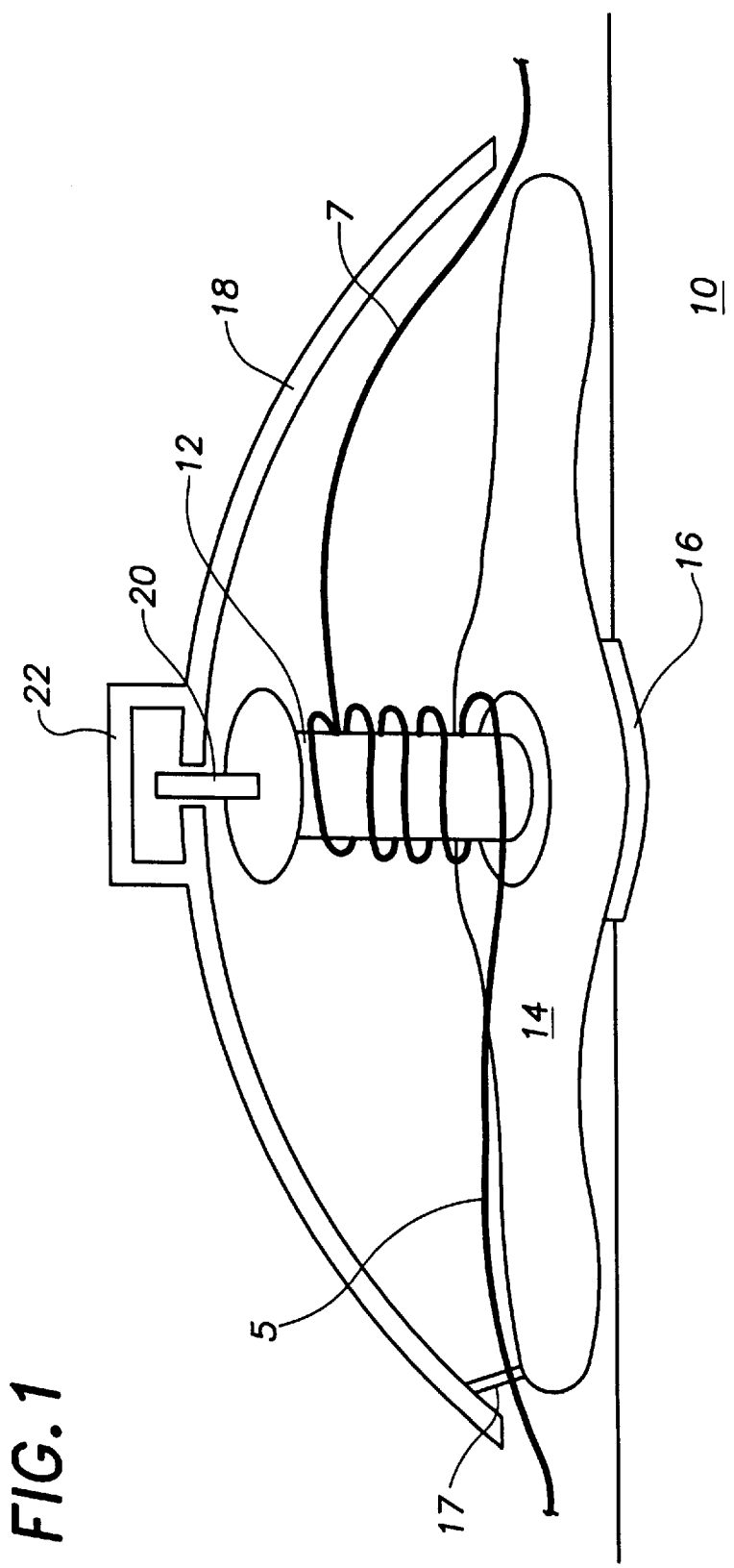
FIG. 1 is a perspective view of the Automatically Retractable Gas Tubing Feed Spool showing the constituent parts.

FIG. 1 shows the Automatically Retractable Gas Tubing Feed Spool. The gas tubing is wound around spool 12, providing a gas supply line 5 and a gas intake line 7. Gas supply line 5 is connected to a cylinder of gas or other supply source and gas intake line 7 provides the feed to the user. The spool 12 is rotatably seated into the base 14 which is fixedly attached to an object 10 by means for fastening 16. The shell 18 is the assembly cover and is removably fastened to the base 14 by a plurality of removable fasteners 17. The assembly is made portable by means of a handle 22 fixedly connected to shell 18. Protruding through the shell 18 is axle 20.

Enabled by this simple and basic embodiment is the operation of the device as follows. Shell 18 covers the entire working assembly and is cast in a single piece from the appropriate material, plastic or aluminum, for instance. Shell 18 is removable from base 14 for access to the spool 12, such that the tubing may be removed and otherwise serviced. Removable fasteners 17 are encircled around base 14 and are comprised of notch and groove connectors, bolts or any other similar linking mechanism. Spool 12 rotates within the shell 18 about the axle 20, thereby dispensing the tubing to the user.

Figure 2:
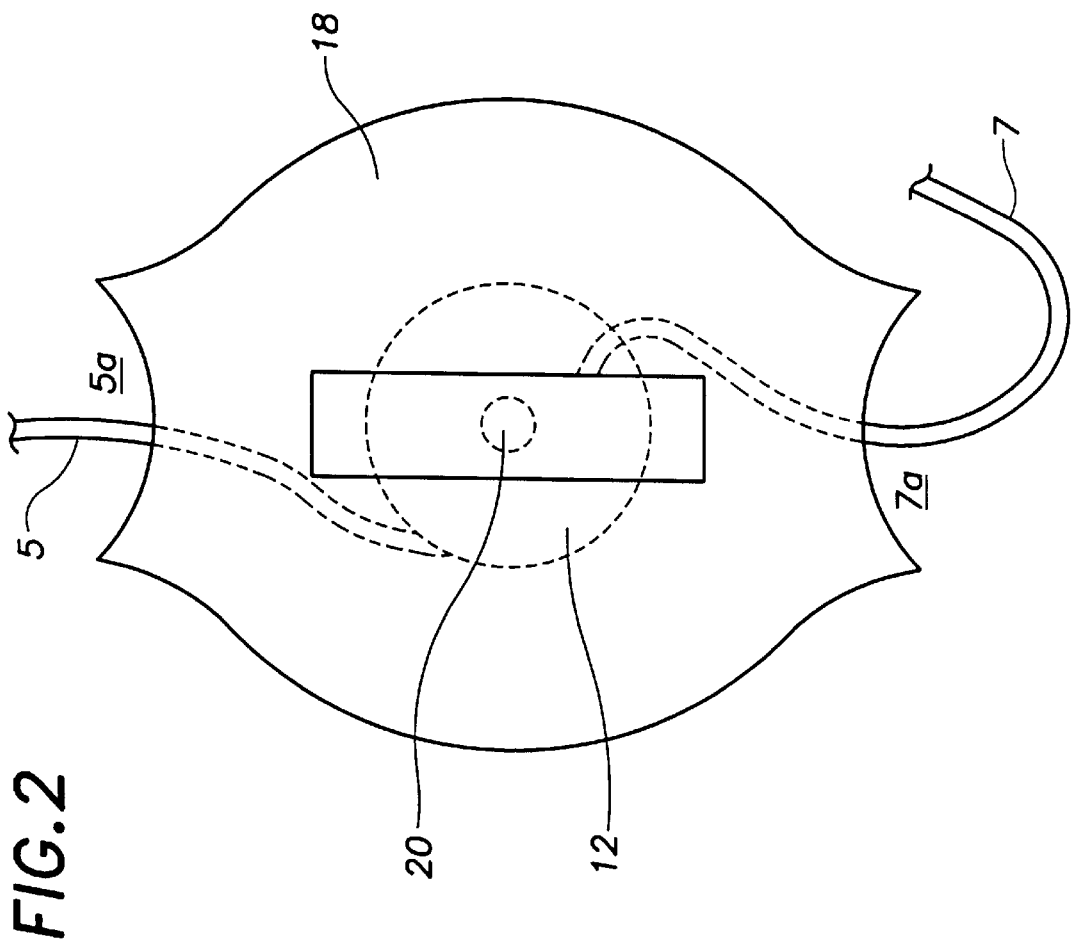
FIG. 2 is a top view of the Automatically Retractable Gas Tubing Feed Spool showing the constituent parts.

FIG. 2 shows the Automatically Retractable Gas Tubing Feed Spool from the top view, with gas supply line 5 and a gas intake line 7 protruding between the shell 18 and the base (See FIG. 1) through the respective ports 5a and 7a. Shown also are spool 12, handle 22 and axle 20.

Figure 3:
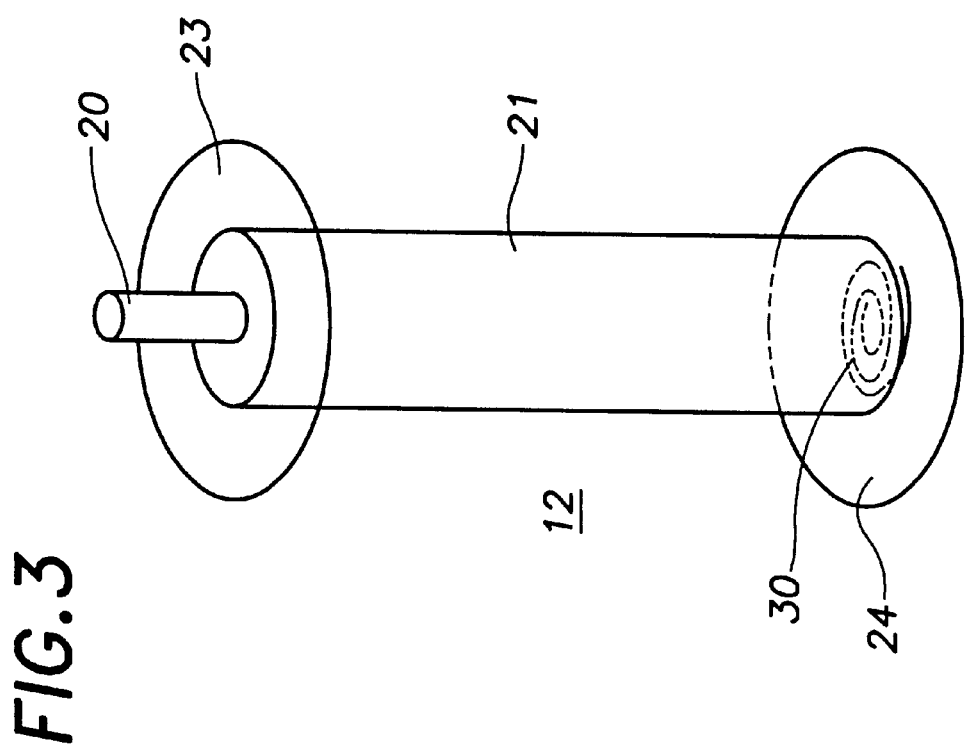
FIG. 3 is a view of the Spool for the Automatically Retractable Gas Tubing Feed Spool showing the spool and coil spring.

FIG. 3 shows the spool 12 and its constituent assembly components. The spool 12 is comprised of upper spool flange 23 and lower spool flange 24 on opposing ends of hollow reel cylinder 21 which acts as the spool piece upon which gas tubing is wound. The spring coil 30 is seated in a lower housing (FIG. 4) of the base. The operation of the spring coil 30 can be visualized accordingly.

Figure 4:
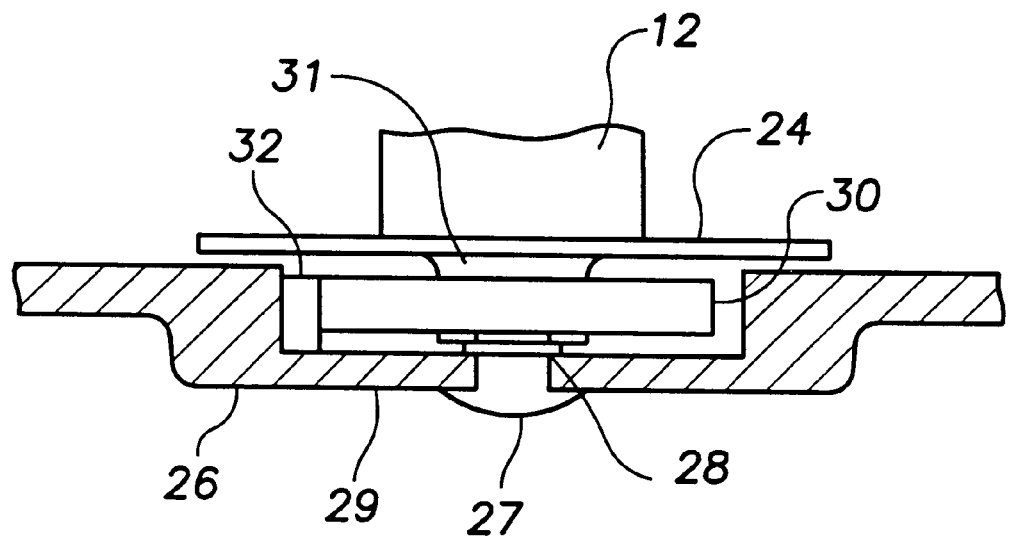
FIG. 4 is a view of the Spool, seated in the lower housing.

FIG. 4 is a view of the spool 12 with lower spool flange 24 seated in the lower housing 26. Lower stub shaft 27 with an E-clip washer 28 provides a means of allowing spool 12 to rotate in the lower housing 26. Lower housing 26 has a spring cavity 29 in which is retained the retracting spring 30. Retracting spring 30 is engaged about the spool 12 below the lower spool flange 24 on lower spool boss 31. A spring-to-housing pin connection 32 fixedly connects the retracting spring 30 to the lower housing 26.

Figure 5:
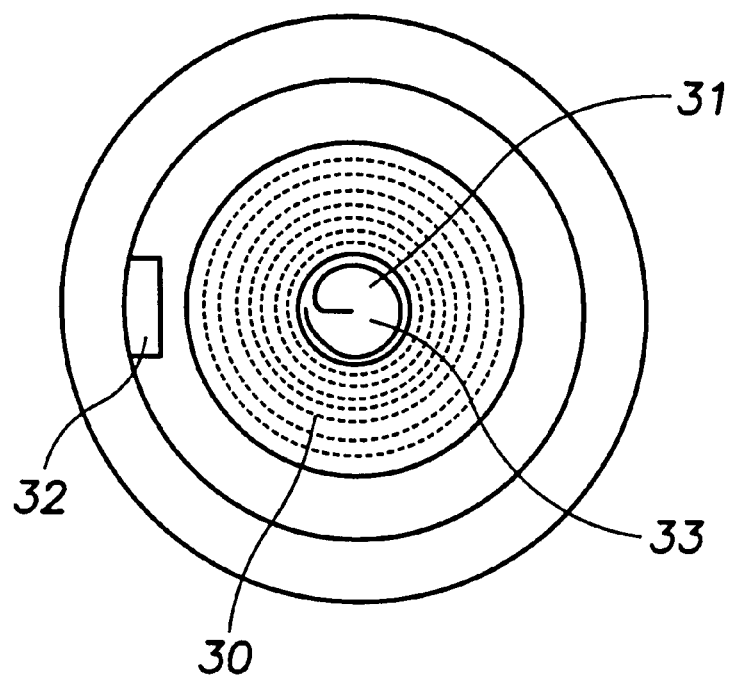
FIG. 5 is a top view of the lower housing with the spring cavity.

FIG. 5 is a top view of the spring-to-housing pin connection 32, the retracting spring 30 and the spring tail 33 rigidly connected in the lower spool boss 31.

Figure 6:
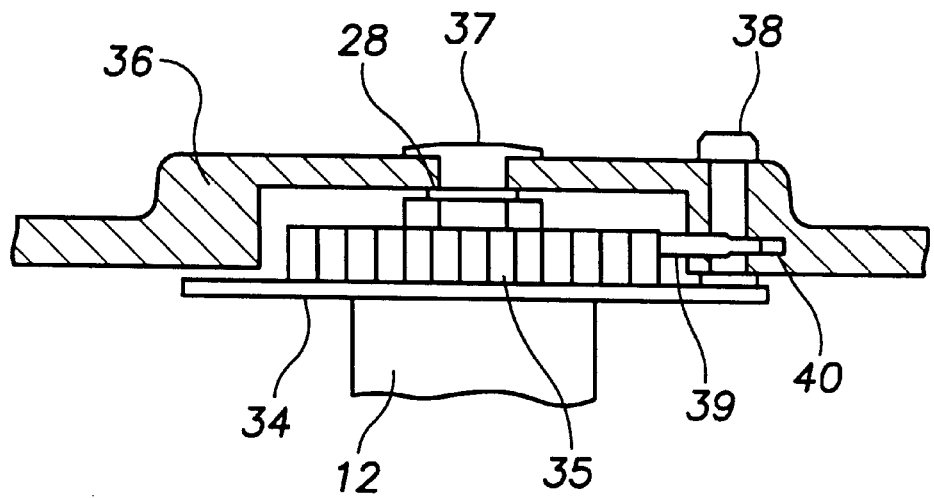
FIG. 6 is view of the spool, seated in the upper housing.

FIG. 6 is a view of the spool 12 with upper spool flange 34 supporting latch gear 35 which is rotatably contained within the upper housing 36 by means of the upper stub shaft 37 and E-clip washer 28. Shown also is the release slide 38 which is actuated by the retraction button (FIG. 2) to control the feed and retraction of the tubing. The release slide 38 actuates the latching plunger 39, which engages the latch gear 35 and is retained by latch spring 40 within the upper housing 36.

The mechanism is thereby demonstrated by viewing the upper housing (FIG. 6) in conjunction with the lower housing (FIG. 4).

Figure 7:
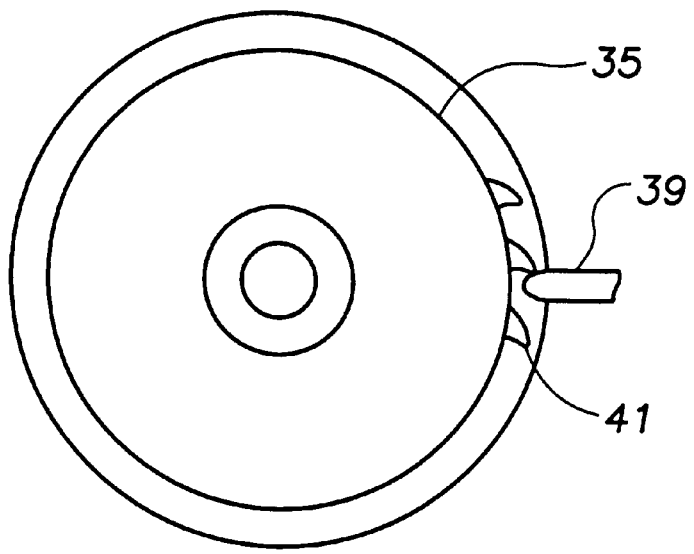
FIG. 7 is a top view of the upper housing with upper stub shaft and release slide.

FIG. 7 is a top view of the latch gear 35 having a plurality of gear teeth 41, which are engaged by the latching plunger 39.

Figure 8:
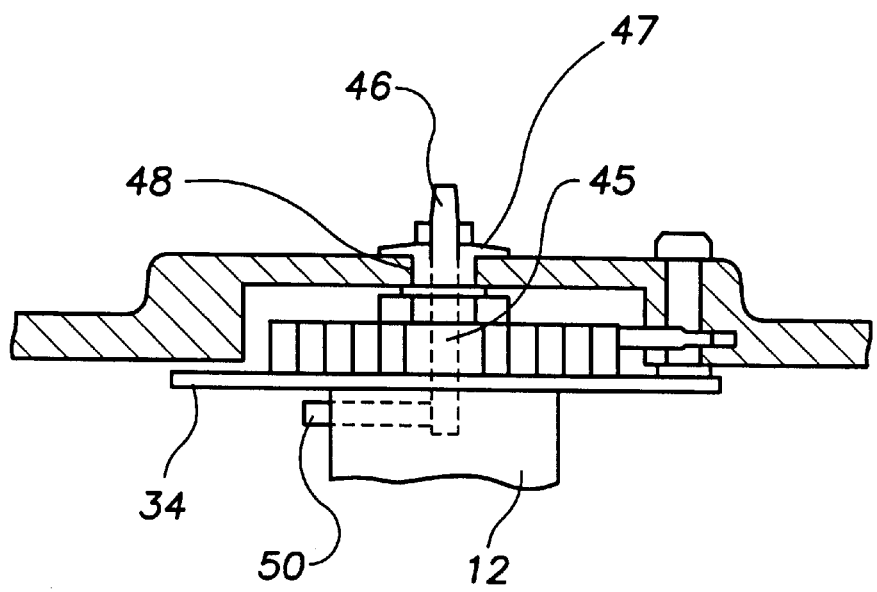
FIG. 8 is an alternative embodiment of the upper housing showing a hose barb swivel for connecting the tubing through the spool.

FIG. 8 demonstrates an alternative embodiment of the present invention whereby the gas supply is coupled to the user by means of an L-couple 45 which penetrates the upper housing 36 and the spool 12 and rotates as the tubing is fed and retracted, as follows. The L-couple 45 has hose barb swivel 46, which connects to the inlet hose (not shown). It is contained within upper housing 36 by snap ring 47, and is rotatably cushioned by bushing 48. Opposite side feed to the supply tubing (not shown) is provided through the 90-degree hose barb 50.

I claim:

1. An Automatically Retractable Gas Tubing Feed Spool for use as a portable conveyer of air from a source, through air tubing, to a user who requires oxygen therapy, comprising:

(a) a slightly flattened and elongated, curved and oval-shaped shell having a long axis and a short axis, with an inner concave surface and an outer convex surface, and having a first perforation at its center and a second perforation adjacent to said first perforation, and having an outlet port on one end of said long axis and an inlet port on the opposite end of said long axis, further comprising:

(i) a handle at its center on said convex surface disposed above said first perforation, and having said second perforation situated adjacent to said handle; and, (ii) a plurality of male means for connection around the periphery of said shell;

(b) a flat base having an inner face and an outer face and having the same length and width as said shell, and having a circular cavity at its center within its inner face, and having a hole through said base at said center of said circular cavity, and having around its periphery a plurality of female means for connection, whereby said male means for connection are seated in respective female means for connection, thereby removably joining said shell and said base;

(c) a cylindrically-shaped spool disposed between said shell and said base, and having an axle disposed longitudinally therein, whereby said axle has an upper projection from said spool and a lower projection from said spool, and having said upper projection from said spool disposed through said first perforation, and having said lower projection disposed through said hole in said center of said circular cavity, and further comprising:
- (i) an upper spool flange disposed about said upper projection of said axle adjacent said concave inner shell, and having a plurality of gear teeth on its periphery;
- (ii) a lower spool flange disposed about said lower projection of said axle; and,
- (iii) a coil of said air tubing wound around said spool, whereby said air tubing exits said outlet port to said user and exits said inlet port to said air source;

(d) a flat circular coil spring with a center fastening point and an outer fastening point, said coil spring being disposed within said circular cavity of said base and fixedly attached to said base at said outer fastening point, and having disposed within its center said lower projection of said axle, and having said lower projection of said axle fixedly joined at said center fastening point, whereby rotation of said spool from a resting position as air tubing is conveyed through said inlet port, on demand of said user, compresses said coil spring, storing rotational energy in said coil spring, and whereby a release of said rotational energy returns said spool to a resting position, thereby drawing said air tubing in through said inlet port and around said spool;

(e) a means for ratcheting having a latching plunger with an engaging end and a protruding end, said engaging end disposed into said gear teeth on said upper spool, whereby said engaging end allows rotation of said spool as said coil spring compresses, and having said protruding end disposed through said second perforation in said shell, whereby depression of said protruding end releases said engaging end from said gear teeth, thereby releasing said rotational energy; and, (f) a means for securing said base to a mobile object on said outer face of said base whereby said Retractable Gas Tubing Feed Spool is removably fastened to, and transportable with, said mobile object.

2. The Automatically Retractable Gas Tubing Feed Spool as claimed in claim 1, further comprising a shell, base and spool made from hard plastic.

3. The Automatically Retractable Gas Tubing Feed Spool as claimed in claim 1, further comprising a shell, base and spool made from aluminum.

4. The Automatically Retractable Gas Tubing Feed Spool as claimed in claim 1, further comprising an L-shaped couple having an articulating joint disposed between perpendicular legs of said couple and having one leg of said couple disposed through said upper projection and the other leg of said couple disposed through said spool, whereby said couple rotates as said spool rotates, and having said air tubing to said air supply source fixedly connected to said leg disposed through said upper projection and having said air tubing to said user fixedly connected to said leg disposed through said spool, whereby said air tubing unwinds from said spool as said coil spring compresses.

* * * * *